United States Patent
Chung et al.

(10) Patent No.: US 8,475,633 B2
(45) Date of Patent: Jul. 2, 2013

(54) PRODUCTION METHOD FOR A NANOPATTERNED EPOXY SUBSTRATE

(75) Inventors: Kwang Hoe Chung, Seongnam-si (KR); Sung Yu Hong, Seoul (KR); Hyun Ju Doh, Seoul (KR); Jin Sub Choi, Bucheon-si (KR); Jae Hoon Lim, Incheon (KR); Sung Joong Kim, Bucheon-si (KR)

(73) Assignee: BioBud Co., Ltd., Seoul (KR)

( * ) Notice: Subject to any disclaimer, the term of this patent is extended or adjusted under 35 U.S.C. 154(b) by 250 days.

(21) Appl. No.: 13/056,922

(22) PCT Filed: Apr. 14, 2009

(86) PCT No.: PCT/KR2009/001916
§ 371 (c)(1),
(2), (4) Date: Jan. 31, 2011

(87) PCT Pub. No.: WO2009/157646
PCT Pub. Date: Dec. 30, 2009

(65) Prior Publication Data
US 2011/0155591 A1      Jun. 30, 2011

(30) Foreign Application Priority Data

Jun. 25, 2008  (KR) ................... 10-2008-0059987

(51) Int. Cl.
    *C23C 14/08*   (2006.01)
(52) U.S. Cl.
    USPC ............ 204/192.1; 204/298.4; 205/105; 205/135; 205/157; 205/205
(58) Field of Classification Search
    USPC ... 204/192.1, 298.1, 298.2, 434, 492; 205/50, 205/80, 105, 135, 157, 205; 156/245
    See application file for complete search history.

(56) References Cited

U.S. PATENT DOCUMENTS

| | | | |
|---|---|---|---|
| 2005/0258522 A1* | 11/2005 | En et al. ................... | 257/670 |
| 2006/0289351 A1 | 12/2006 | Xiao et al. | |
| 2009/0196936 A1 | 8/2009 | John et al. | |

OTHER PUBLICATIONS

Lim et al., "Titanium Oxide Nanowires Originating from Anodically Grown Nanotubes: The Bamboo-Splitting Model," Small 9:1504-1507, 2007.
Mor et al., "A Review on Highly Ordered, Vertically Oriented TiO$_2$ Nanotube Arrays: Fabrication, Material Properties, and Solar Energy Applications," Solar Energy Materials & Solar Cells 90:2011-2075, 2006.
International Search Report from International Application No. PCT/KR2009/001916, dated Nov. 23, 2009 (date of completion of search) and Nov. 24, 2009 (date of mailing of report).
Written Opinion from International Application No. PCT/KR2009/001916, dated Nov. 24, 2009.
International Preliminary Report on Patentability from International Application No. PCT/KR2009/001916, dated Jan. 18, 2011.

* cited by examiner

*Primary Examiner* — Keith Hendricks
*Assistant Examiner* — Susan D Leong
(74) *Attorney, Agent, or Firm* — Clark & Elbing LLP

(57) ABSTRACT

Provided is a method for preparing an epoxy substrate having a nanopattern, including: (a) forming a titanium oxide film by anodizing a titanium substrate; (b) obtaining a titanium substrate having a concave shape formed on the surface by removing the titanium oxide film from the titanium substrate on which the titanium oxide film has been formed; (c) coating an epoxy resin onto the titanium substrate on which the concave shape has been formed; and (d) obtaining an epoxy substrate having a nanopattern of convex surfaces by removing the titanium substrate.

12 Claims, 7 Drawing Sheets

PRODUCTION METHOD FOR A NANOPATTERNED EPOXY SUBSTRATE

CROSS-REFERENCE TO RELATED APPLICATIONS

This application is the U.S. national stage filing under 35 U.S.C. §371 of international application PCT/KR2009/001916, filed Apr. 14, 2009, which claims priority from Korean Patent Application No. 10-2008-0059987, filed Jun. 25, 2008.

TECHNICAL FIELD

The present disclosure relates to a method for preparing an epoxy substrate having a nanopattern, an epoxy substrate for measuring blood coagulation prepared by the method, and method for measuring blood coagulation using the epoxy substrate.

BACKGROUND ART

In case of abnormal bloodstream caused by blood clots, such as deep vein thrombosis, pulmonary embolism, artificial heart valve implantation, atrial fibrillation, etc., anticoagulation treatment is required. These patients should be continuously monitored for anticoagulant intake in order to prevent bleeding or embolism. A blood coagulation test is carried out to verify whether blood coagulation occurs normally in the body (1).

In general, the blood coagulation test is based on transmittance of light. When the blood plasma of a patient in liquid state is mixed with a test reagent, light transmittance decreases as the blood plasma coagulates, which is measured dynamically (2). However, the current blood coagulation test carried out in the central diagnostic unit of a hospital using large test instruments is time-consuming, requires a hospital visit, and needs a large volume of blood.

Especially, the existing instruments could not be used by ordinary people because they require analysis by medical experts.

The inventors of the present disclosure have developed a technique for preparing a new-concept test substrate capable of resolving these inconveniences. By providing a nanopatterned epoxy substrate prepared by electrochemically anodizing a titanium substrate, the surface area for test is improved along with sensitivity. As a result, a blood coagulation test is possible even with a small-volume sample.

Throughout the specification, a number of publications and patent documents are referred to and cited. The disclosure of the cited publications and patent documents is incorporated herein by reference in its entirety.

DISCLOSURE

The inventors have made efforts to develop a substrate for measurement of blood coagulation allowing to ascertain whether blood coagulation occurs normally in the body. As a result, they have found out that an epoxy substrate having a nanopattern of convex surfaces prepared by coating an epoxy resin onto a nanopattern of a concave shape formed on the surface of an anodized titanium substrate, removing the titanium substrate, and then forming a metal electrode thereon may be used for electrochemical measurement of blood coagulation, since the blood coagulation can be detected through change in resistance.

The present disclosure is directed to providing a method for preparing an epoxy substrate having a nanopattern.

The present disclosure is also directed to providing an epoxy substrate for measuring blood coagulation prepared by the method.

The present disclosure is also directed to providing a method for measuring blood coagulation using the epoxy substrate.

Other features and aspects will be apparent from the following detailed description, the drawings, and the claims.

DESCRIPTION OF DRAWINGS

The above and other objects, features and advantages of the present disclosure will become apparent from the following description of certain exemplary embodiments given in conjunction with the accompanying drawings, in which:

FIG. 12a and FIG. 12b are graphs showing a result of prothrombin time (PT) measurement for PPP (FIG. 12a) and WB (FIG. 12b) using a nanopatterned epoxy substrate according to the present disclosure (The broken lines are results obtained with an existing coagulation electrode (graphite electrode). In FIG. 12a, PT reagent was treated with 2, 1 and 3 μL, from one exhibiting the highest voltage at 180 seconds among the broken lines, and with 1, 2 and 3 μL, from one showing the fastest voltage change among the solid lines. In FIG. 12b, PT reagent was treated with 5, 3 and 1 μL, from one exhibiting the highest voltage at 180 seconds among the broken lines, and with 3, 5 and 1 μL, from one showing the fastest voltage change among the solid lines.).

BEST MODE

Hereinafter, the embodiments of the present disclosure will be described in detail with reference to accompanying drawings.

In an aspect, present disclosure provides a method for preparing an epoxy substrate having a nanopattern, comprising: (a) forming a titanium oxide film by anodizing a titanium substrate; (b) obtaining a titanium substrate having a concave shape formed on the surface by removing the titanium oxide film from the titanium substrate on which the titanium oxide film has been formed; (c) coating an epoxy resin onto the titanium substrate on which the concave shape has been formed; and (d) obtaining an epoxy substrate having a nanopattern of convex surfaces by removing the titanium substrate.

The inventors have made efforts to develop a substrate for measurement of blood coagulation allowing to ascertain whether blood coagulation occurs normally in the body. As a result, they have found out that an epoxy substrate having a nanopattern of convex surfaces prepared by coating an epoxy resin onto a nanopattern of a concave shape formed on the surface of an anodized titanium substrate, removing the titanium substrate, and then forming a metal electrode thereon may be used for electrochemical measurement of blood coagulation, since the blood coagulation can be detected through change in resistance.

The method for preparing a nanopatterned epoxy substrate according to the present disclosure will be described in detail.

Formation of Titanium Oxide Film

A titanium oxide film is formed by anodizing a titanium substrate.

Before the anodization, the titanium substrate may be pretreated by rinsing. Various rinsing solutions known in the art may be used for the pretreatment.

As used herein, "anodization" refers to a process whereby a metal substrate is connected to an anode and a platinum (Pt) electrode is connected to a cathode in an electrolyte solution, and an appropriate voltage is applied, so that a nanoporous metal oxide film with regular arrangement is formed on the surface of the metal substrate.

In an embodiment of the present disclosure, the anodization is performed in an electrolyte solution. The electrolyte solution may include various electrolyte solutions known in the art. Specifically, ammonium fluoride/ethylene glycol may be used.

In a specific embodiment of the present disclosure, the anodization is performed by applying a voltage of 20-60 V.

Obtainment of Titanium Substrate Having Concave Shape

The titanium oxide film may be removed by various methods known in the art. Specifically, after coating an epoxy, the titanium oxide film attached to the epoxy may be separated based on the difference in surface energy between the epoxy with the titanium oxide film attached and the titanium substrate.

When the titanium oxide film is removed, a titanium substrate having a concave shape formed on the surface may be obtained.

Coating of Epoxy Resin

After the titanium oxide film is removed, an epoxy resin may be coated onto the titanium substrate on which the concave shape has been formed to prepare an epoxy substrate having a nanopattern.

In accordance with the present disclosure, by coating the epoxy resin onto the titanium substrate from which the titanium oxide film has been removed, a nanopattern of convex surfaces may be formed on the epoxy resin.

Obtainment of Epoxy Substrate Having Nanopattern of Convex Surfaces

Thereafter, the titanium substrate is removed. The titanium substrate may be removed various methods known in the art. Specifically, after coating an epoxy onto the titanium nanopattern with the oxide film (nanotube) removed, the titanium oxide film may be removed based on the difference in surface energy between the hardened epoxy and the titanium substrate.

When the titanium substrate is removed, a nanopattern of convex surfaces is formed on the epoxy substrate on which the concave shape has been formed. As such, by forming the nanopattern of convex surfaces, the surface area of the epoxy substrate may be maximized.

Formation of Metal Electrode on Epoxy Substrate

In a specific embodiment of the present disclosure, a metal electrode may be formed on the epoxy substrate having the nanopattern.

In another specific embodiment of the present disclosure, the metal may be gold, silver, copper or platinum. More specifically, it may be gold or silver. Most specifically, it may be gold.

The formation of the metal electrode on the epoxy substrate having the convex shape may be performed by various methods known in the art. Specifically, electron beam deposition, vacuum deposition, thermal evaporation, sputtering, low-pressure chemical vapor deposition, sol-gel synthesis, electroplating or electroless plating may be employed. More specifically, common physical evaporation techniques, such as thermal evaporation, spin coating, vacuum deposition or sputtering, may be employed. Most specifically, vacuum deposition or sputtering may be employed.

Provision of Mask Having Hole on Metal Electrode

In a specific embodiment of the present disclosure, a mask having a hole may be provided on the metal electrode. The mask is provided on the epoxy substrate so as to allow the electrochemical reaction to occur on the same area.

In another aspect, the present disclosure provides an epoxy substrate for measuring blood coagulation having a nanopattern prepared according to the above-described methods.

Since the epoxy substrate for measuring blood coagulation having a nanopattern according to the present disclosure is prepared by the afore-described method, a detailed description thereof will be omitted to avoid unnecessarily obscuring the present disclosure.

In another aspect, the present disclosure provides a method for measuring blood coagulation using the epoxy substrate prepared according to the present disclosure as described above.

The method for measuring blood coagulation according to the present disclosure comprises: contacting a blood sample with the epoxy substrate having a nanopattern prepared according to the present disclosure; and measuring voltage of the epoxy substrate.

In a specific embodiment of the present disclosure, the blood sample may be platelet-poor plasma or whole blood.

When a blood sample is dropped on the epoxy substrate prepared according to the present disclosure, electrical current flows as the platelet-poor plasma or whole blood serves as an electrolyte. However, when the platelet-poor plasma or whole blood is coagulated, the current flow is interrupted and resistance increases. By measuring this change, it can be ascertained whether blood coagulation occurs normally in the body.

MODE FOR INVENTION

The examples and experiments will now be described. The following examples and experiments are for illustrative purposes only and not intended to limit the scope of the present disclosure.

Test Materials and Methods

Example 1

Pretreatment of Titanium Substrate

A titanium substrate (thickness: 0.25 mm, purity: 99.6%, diameter: 15 mm, Goodfellow) was rinsed using an ultrasonic cleaner (Power Sonic 505, Hwashin Tech) with acetone (99.5%, Samchun Chemical) for 15 minutes, and then with triple distilled water (Human Power I+Pure Water System, Human Power, RO 0 μs/cm, UP 18.3 MΩ·cm).

Example 2

Preparation of Anodizing Cell

Figure 1:
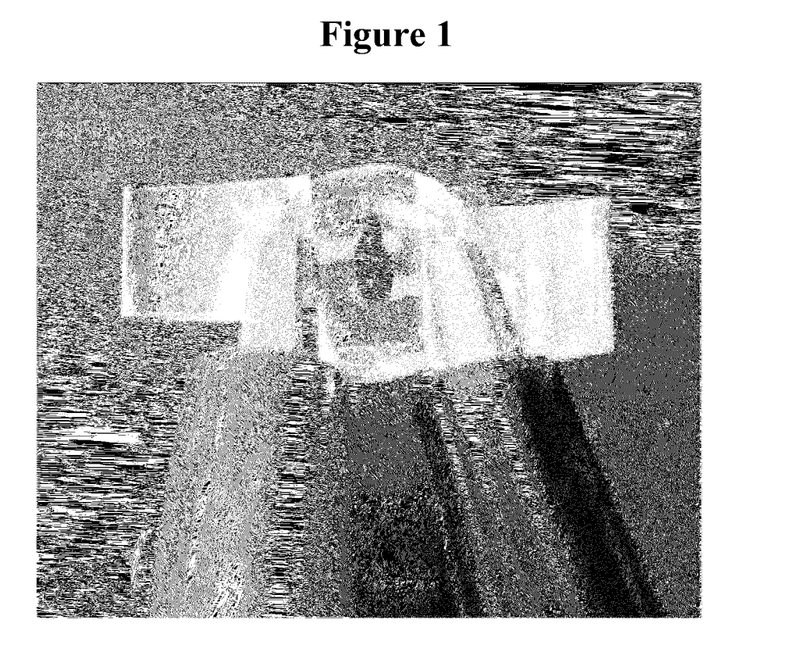
FIG. 1 shows measurement of blood coagulation using a nanopatterned epoxy substrate of the present disclosure (An electrode is connected to copper tapes on both sides and, after dropping platelet-poor plasma or whole blood on a masking tape, voltage is measured while flowing a constant current of 0.01 mA.)
Figure 2:
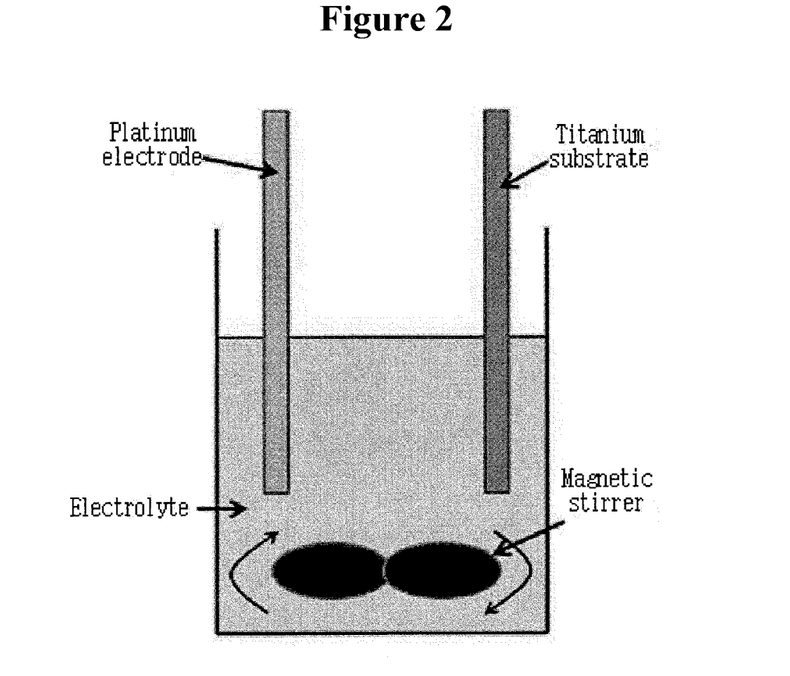
FIG. 2 schematically shows anodization of a titanium substrate according to the present disclosure (Metallic titanium and platinum are connected to the anode and the cathode, respectively. The electrolyte is 0.25 wt % ammonium fluoride/ethylene glycol.)

As illustrated in FIG. 2, an anodizing cell used in this example consisted of a titanium substrate, a counter electrode (platinum wire, thickness: 0.2 mm, purity: 99.9%, Goods Token) and an electrolyte (0.25 wt % ammonium fluoride/ ethylene glycol). A stirring bar was set to rotate about 500 times per minute in order to stir the electrolyte, so as to facilitate the reaction and allow heat produced on the substrate surface to spread into the electrolyte.

The electrolyte comprised 0.25 wt % ammonium fluoride (98%, A.C.S. reagent, Sigma-Aldrich)/ethylene glycol (anhydrous, 99.8%, Sigma-Aldrich).

Example 3

Anodizing Reaction

A two-electrode system that can be directly applied to an actual process was used to apply a voltage to the cell of Example 2. Anodizing reaction was carried out at room temperature for 5 hours while applying a voltage of 40 V using Source Meter (Model: 2400, Keithley) as the two-electrode system. Then, after rinsing the titanium substrate with rinsing water, a self-aligned titanium nanotube was obtained. National Instruments Lab View 6.1 software was used in KE2400 constant mode.

Example 4

Removal of Oxide Film after Anodizing Reaction

Figure 3:
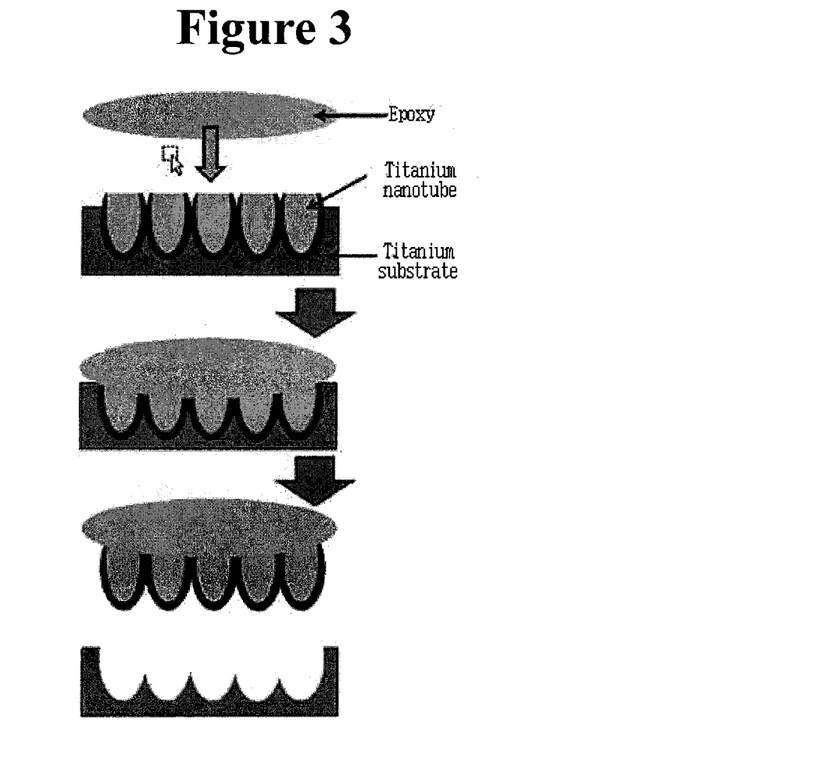
FIG. 3 schematically shows separation of a titanium nanotube prepared by anodization from a titanium substrate using an epoxy according to the present disclosure.
Figure 4:
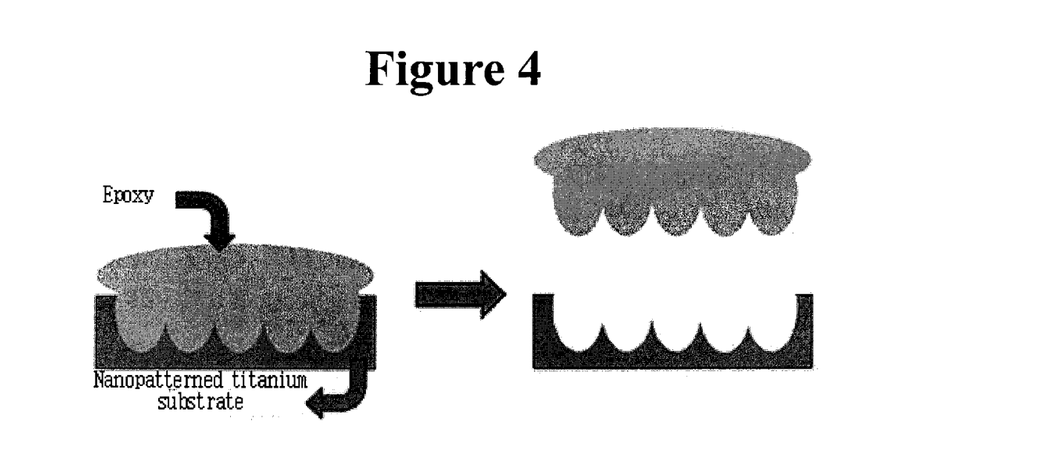
FIG. 4 shows preparation of a nanopatterned epoxy substrate using a nanopatterned titanium substrate prepared by anodization according to the present disclosure.
Figure 5:
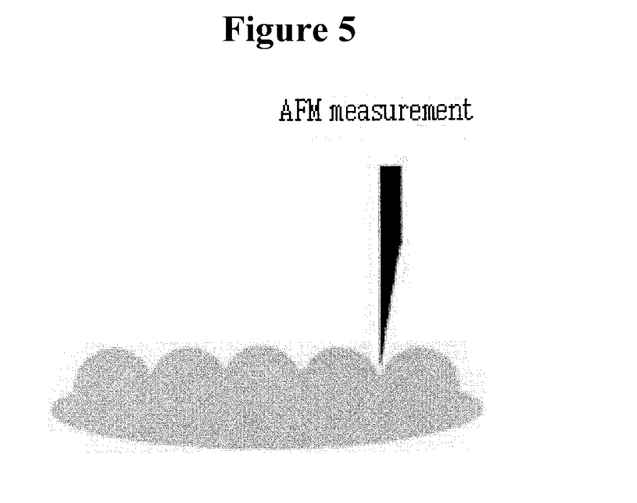
FIG. 5 shows measurement of a nanopatterned epoxy substrate of the present disclosure by atomic force microscopy (AFM) (The epoxy substrate is separated from a nanopattern titanium substrate, and the nanopattern of the epoxy substrate is analyzed by AFM.)

An epoxy (Formica, Dongil Lab Mate, epoxy: hardener=10:1) was poured on the titanium nanotube prepared by the anodization. After the epoxy was hardened, the hardened epoxy was detached to remove the oxide film. When the epoxy is applied onto the titanium nanotube, the epoxy penetrates into the nanotube and binds with the oxide film. Since the binding energy is larger than the surface energy of the titanium substrate, the epoxy bound to the oxide film may be easily separated from the titanium substrate. This is schematically illustrated in FIG. 3.

Example 5

Figure 6:
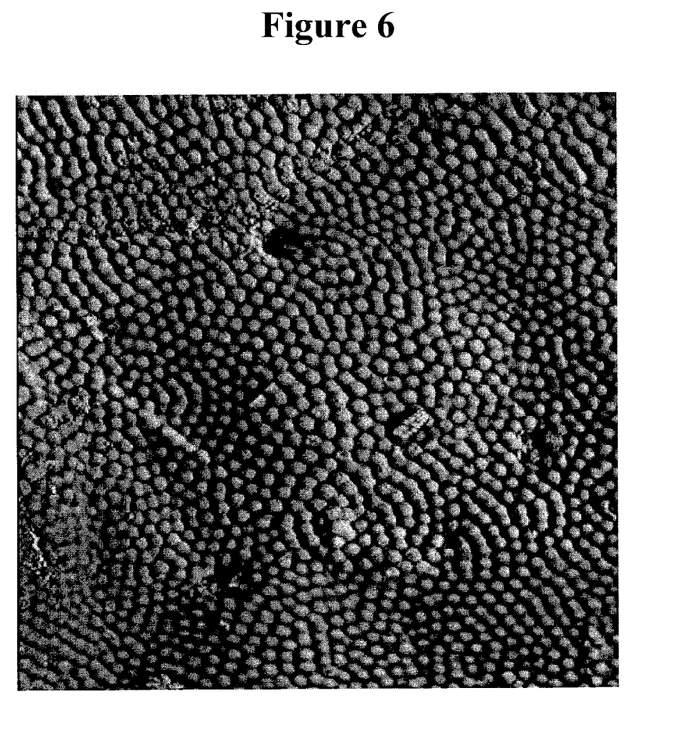
FIG. 6 is an AFM image showing the surface of a nanopatterned epoxy substrate of the present disclosure (In the absence of coating with gold particles, a double embossing structure is shown. A pattern with a height of 40 nm and a diameter of 100 nm is identified.)

Preparation of Nanopatterned Epoxy Substrate Using Nanopatterned Titanium Substrate A 10:1 mixture of an epoxy and a hardener based on weight was coated onto the titanium substrate having a concave-shaped nanopattern resulting from the removal of the oxide film in Example 4. Subsequently, the epoxy was separated from the titanium substrate to obtain an epoxy substrate having a convex-shaped nanopattern. Since the titanium substrate with the oxide film (nanotube) removed has the concave-shaped nanopattern, the epoxy substrate having a convex-shaped nanopattern is easily obtained by pouring the epoxy onto the titanium substrate and then removing the epoxy. FIG. 6 is an atomic force microscopic (AFM) image showing the surface of thus prepared nanopatterned epoxy substrate.

Example 6

Formation of Electrode on Nanopatterned Epoxy Substrate

A conductive epoxy (Dotite electroconductives, type D-500, Dongil Lab Mate) was applied on the nanopatterned epoxy substrate prepared in Example 5, at the portions where copper tapes would be connected. Then, gold (Au, purity: 99.99%, Dongil Lab Mate) was coated on the connection portions into a desired electrode shape using vacuum deposition apparatuses (a sputter and an evaporator, Vacuum Device Inc, Vacuum Device Ion Coater System, Magnetron Sputter, MSP-1S) while flowing a current of 40 mA. The current of 40 mA was selected to control the size of the coated gold particles to 10 nm. Then, copper tapes were connected to the portions where the electrodes were formed on the nanopatterned epoxy substrate.

Figure 7:
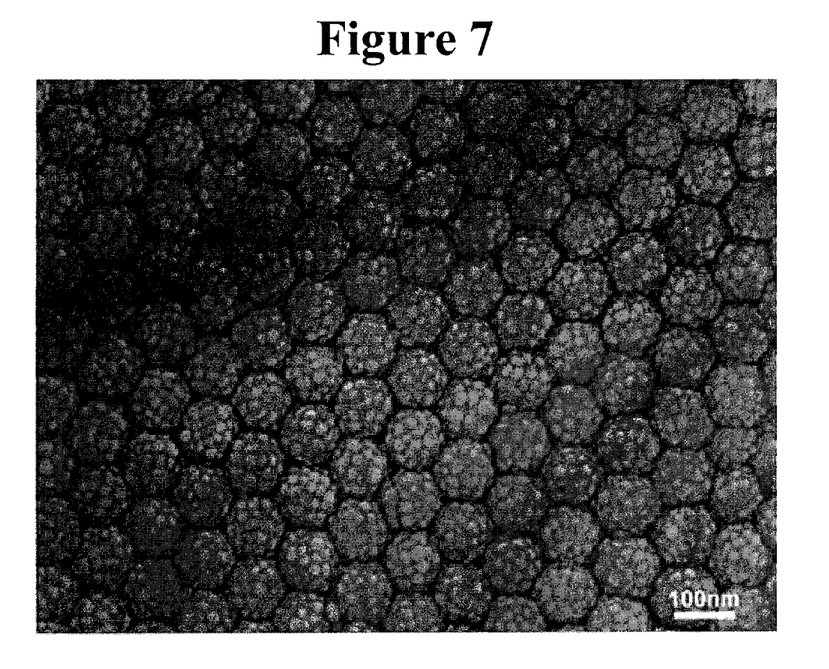
FIG. 7 is a field emission scanning electron microscopic (FE-SEM) image showing the surface of a nanopatterned titanium substrate prepared by anodization according to the present disclosure, with gold particles coated thereon.

FIG. 7 is a field emission scanning electron microscopic (FE-SEM) image showing the surface of the nanopatterned titanium substrate. A triple embossing structure is identified. The triple embossing structure consists of an embossing structure of several micrometers formed at the grain boundary of the titanium nanopattern, a nanostructure of a diameter of 100 nm, and gold particles of a diameter of about 10 nm formed thereon.

Example 7

Provision of Mask on Electrode of Nanopatterned Epoxy Substrate

Figure 11:
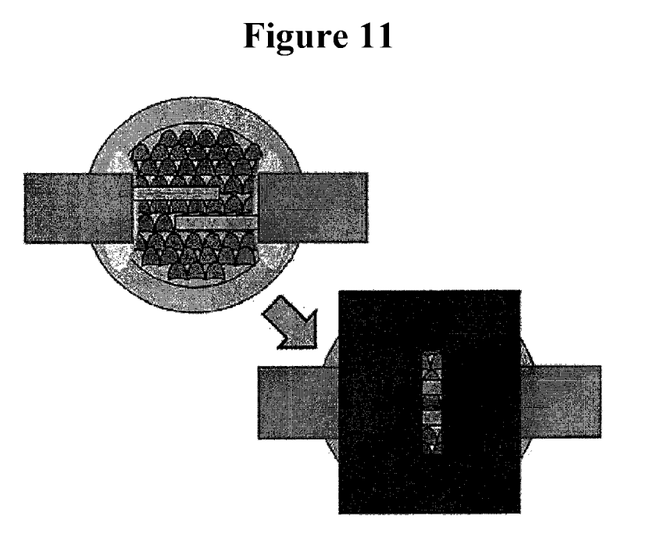
FIG. 11 schematically shows a mask on which PPP or WB contacts with an electrode of a nanopatterned epoxy substrate according to the present disclosure.

A rectangular mask of 3 mm×5 mm was provide on the nanopatterned epoxy substrate on which the electrode had been formed in Example 6, such that electrochemical reaction could occur on the same area. The mask was made of an insulating hydrophobic polymer tape with good adhesivity (Kapton tape), so that platelet-poor plasma (PPP) or whole blood (WB) could not leak out of the reaction area. FIG. 11 schematically shows the mask provided on the nanopatterned epoxy substrate. Since the PPP or WB can react only on the same area, a reproducible measurement result is ensured.

Example 8

Electrochemical Detection of Blood Coagulation Using Nanopatterned Epoxy Substrate PPP or WB containing a prothrombin time (PT) reagent (Hemosil PT-Fibrinogen HS, Instrumentation Laboratory, USA) was dropped on the patterned portion of the nanopatterned epoxy substrate. While supplying a constant current of 0.01 mA using Potentiostat/Galvanostat Autolab, coagulation of the PPP or WB was detected based on the change in voltage detected with the software General Purpose Electrochemical System (GPES) version 4.9.

Test Result

Figure 10:
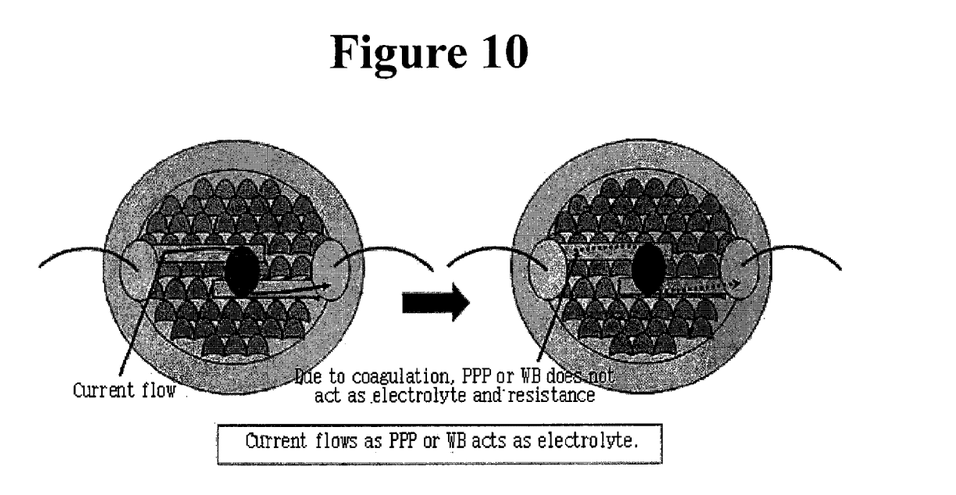
FIG. 10 schematically shows flow of an electrical current on an electrode of a nanopatterned epoxy substrate according to the present disclosure (The linear arrow represents the direction of current flow. The curved solid arrow represents that current flows as platelet-poor plasma (PPP) or whole blood (WB) acts as electrolyte. The curved broken arrow represents that weak current flows as the PPP or WB does not act as electrolyte because of coagulation.)

As seen from FIG. 10, when a constant current of 0.01 mA is flown, current flows initially as the PPP or WB acted as an electrolyte. Then, when the PPP or WB is coagulated, the current flow is interrupted and resistance increases. The increase in resistance may be plotted against time. The PPP or WB coagulation time can be controlled by adjusting the amount of the PT reagent. The result can be obtained within 40 seconds.

The volume of the PT reagent was 1-3 μL for PPP and 1-5 μL for WB. PT was measured after adding the PT reagent to 20 μL of the PPP or WB.

Figure 12A:
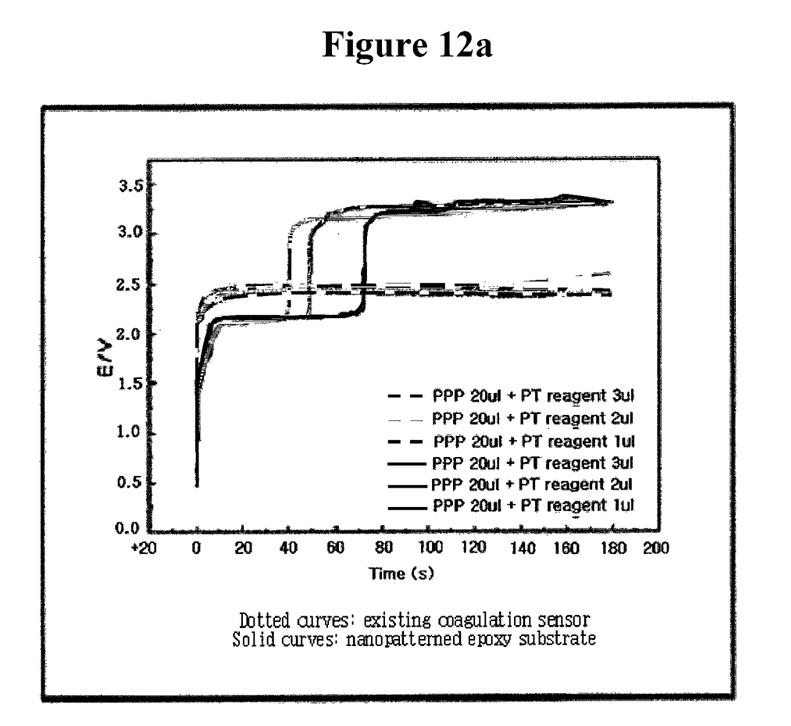

As seen from FIG. 12a, when 1 μL of the PT reagent was added to the PPP, the voltage change was detected at 40 seconds. The voltage change was caused by the increase in resistance under constant current flow. That is to say, the voltage increased as the resistance increased due to the coagulation of the PPP. Thus, the coagulation of the PPP can be represented graphically based on the increase of resistance.

Figure 12B:
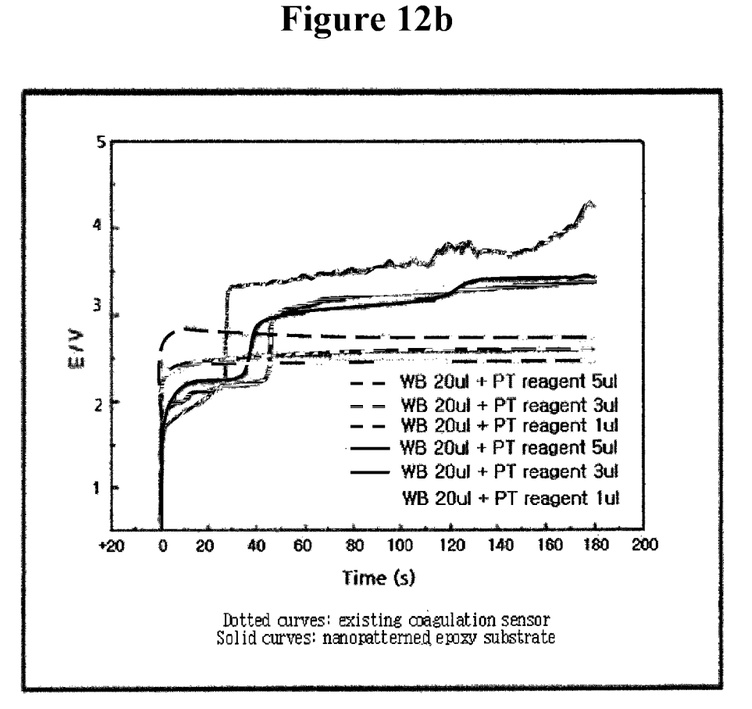

Also, as seen from FIG. 12b, when 2 μL of the PT reagent was added to the WB, the voltage change was detected at about 23 seconds. The voltage increase was caused by the increase in resistance at the surface of the epoxy substrate due to the coagulation of the WB.

Although the coagulation of the PPP or WB could not be detected with the existing coagulation electrode (graphite electrode), it could be distinctly detected with the nanopatterned epoxy substrate according to the present disclosure.

Also, the graphs show that the nanopatterned epoxy substrate according to the present disclosure is capable of coagulation measurement for both the PPP and WB.

Figure 8:
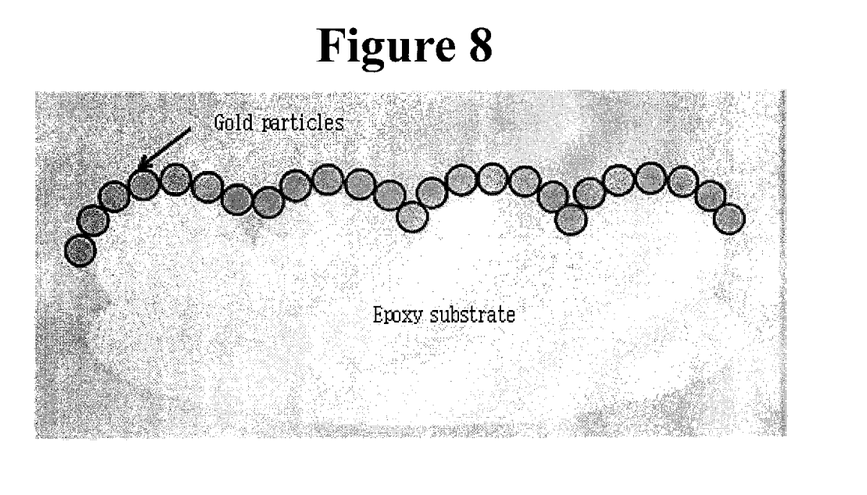
FIG. 8 schematically shows a triple embossing structure of a nanopatterned epoxy substrate prepared according to the present disclosure, with gold particles coated thereon (When gold particles are coated on a nanopattern epoxy having a double embossing structure to form an electrode, a triple embossing structure is attained.)
Figure 9:
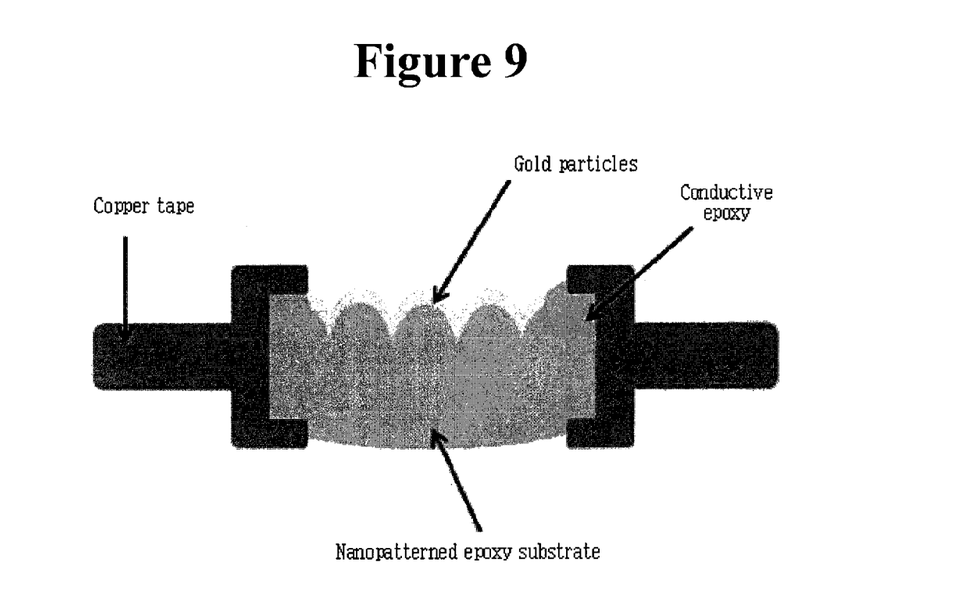
FIG. 9 schematically shows a cross-section of a nanopatterned epoxy substrate according to the present disclosure with an electrode formed thereon (Along with an embossing structure, gold particles forming the electrode, conductive epoxy and copper tapes are shown.)

The distinct change in the voltage, which is not detected with the existing blood coagulation sensor, is a characteristic feature of the nanopatterned epoxy substrate according to the present disclosure. The general graphite electrode used in the existing blood coagulation sensor cannot detect the coagulation of the PPP or WB sensitively because the surface area is not maximized. In contrast, because the nanopatterned epoxy substrate prepared in accordance with the present disclosure has a triple nanopattern structure, as shown in FIG. 8, it has maximized surface area with a nanopattern of diameter 100 nm and height 40 nm. Thus, it is capable of detecting very delicate changes occurring on the surface. As a result, the subtle change that cannot be detected with the existing electrode can be represented graphically.

As described in detail above, the present disclosure provides a method for preparing a nanopatterned epoxy substrate, an epoxy substrate prepared by the method, and a method for measuring blood coagulation using the epoxy substrate. According to the present disclosure, a nanopattern with a concave shape is formed on a titanium substrate by anodizing the titanium substrate. Then, an epoxy substrate having a nanopattern of convex surfaces is prepared by applying an epoxy resin onto the titanium substrate and then removing the titanium substrate. This straightforward process makes it possible to efficiently prepare an epoxy substrate having a nanopattern, which is fine and on the nano scale, for the measurement of blood coagulation. Further, the epoxy substrate prepared in accordance with the present disclosure makes it possible to efficiently use an electrochemical technique to ascertain whether or not blood coagulation is present in a blood sample.

REFERENCES

1. Kovacs M, Cruickshank M, Wells P S. et al. Randomized assessment of a warfarin nomogram for initial oral anticoagulation after venous thromboembolic disease. *Haemostasis.*, 28: 628 (1999).
2. Rossi E, Mondonico P, Lombardi A, Preda L. Method for the determination of functional (clottable) fibrinogen by the new family of ACL coagulometers. *Thromb. Res.* 52: 453-468 (1988).

The present application contains subject matter related to Korean Patent Application No. PCT/KR2009/001916, filed in the Korean Intellectual Property Office on 14 Apr. 2009, the entire contents of which is incorporated herein by reference.

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

The invention claimed is:

1. A method for preparing an epoxy substrate having a nanopattern, comprising:
   forming a titanium oxide film by anodizing a titanium substrate;
   obtaining a titanium substrate having a concave shape formed on the surface by removing the titanium oxide film from the titanium substrate on which the titanium oxide film has been formed;
   coating an epoxy resin onto the titanium substrate on which the concave shape has been formed; and
   obtaining an epoxy substrate having a nanopattern of convex surfaces by removing the titanium substrate.

2. The method according to claim 1, which further comprises, after obtaining the epoxy substrate having a nanopattern of convex surfaces, forming a metal electrode on the epoxy substrate having the nanopattern.

3. The method according to claim 2, which further comprises, after forming the metal electrode on the epoxy substrate, providing a mask having a hole on the metal electrode.

4. The method according to claim 1, wherein the anodization is performed in an electrolyte solution.

5. The method according to claim 4, wherein the electrolyte solution is ammonium fluoride/ethylene glycol.

6. The method according to claim 1, wherein the anodization is performed by applying a voltage of 20-60 V.

7. The method according to claim 1, wherein the removal of the titanium oxide film comprises coating an epoxy and separating the titanium oxide film attached to the epoxy based on the difference in surface energy between the epoxy with the titanium oxide film attached and the titanium substrate.

8. The method according to claim 2, wherein the metal of the metal electrode is gold, silver, copper or platinum.

9. The method according to claim 2, wherein the metal electrode is formed by electron beam deposition, vacuum deposition, thermal evaporation, sputtering, low-pressure chemical vapor deposition, sol-gel synthesis, electroplating or electroless plating.

10. An epoxy substrate for measuring blood coagulation having a nanopattern prepared according to one of the methods of claims 1 to 3.

11. A method for measuring blood coagulation, comprising:

contacting a blood sample with the epoxy substrate having a nanopattern according to claim 10; and measuring voltage of the epoxy substrate.

12. The method for measuring blood coagulation according to claim 11, wherein the blood sample is platelet-poor plasma or whole blood.

\* \* \* \* \*